US00PP17807P2

(12) United States Plant Patent
Lentjes

(10) Patent No.: US PP17,807 P2
(45) Date of Patent: Jun. 12, 2007

(54) ***CHRYSANTHEMUM* PLANT NAMED 'SERGINHO'**

(50) Latin Name: *Chrysanthemum×morifolium*
Varietal Denomination: Serginho

(75) Inventor: Gerard B. M. Lentjes, Kerkdriel (NL)

(73) Assignee: Aalround Agri Management (NL)

( * ) Notice: Subject to any disclaimer, the term of this patent is extended or adjusted under 35 U.S.C. 154(b) by 0 days.

(21) Appl. No.: 11/311,669

(22) Filed: Dec. 19, 2005

(51) Int. Cl.
*A01H 5/00* (2006.01)

(52) U.S. Cl. ..... Plt./289

(58) Field of Classification Search ..... Plt./289
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Serginho', characterized by its upright, outwardly spreading and mounded plant habit; freely branching growth habit; early response time; decorative-type inflorescences with elliptic-shaped ray florets; light yellow-colored ray florets; and good postproduction longevity.

2 Drawing Sheets

Botanical designation: *Chrysanthemum×morifolium.*
Cultivar denomination: 'Serginho'.

BACKGROUND OF THE INVENTION

The present Invention relates to a new and distinct cultivar of *Chrysanthemum* plant, botanically known as *Chrysanthemum×morifolium* and hereinafter referred to by the name 'Serginho'.

The new *Chrysanthemum* is a product of a planned breeding program conducted by the Inventor in Hensbroek, The Netherlands. The objective of the program is to create or discover new potted *Chrysanthemum* cultivars that are suitable for year-round production with uniform and vigorous plant growth and good post-production longevity.

The new *Chrysanthemum* originated from a cross-pollination made on Mar. 21, 2003 in Hensbroek, The Netherlands of a proprietary selection of *Chrysanthemum×morifolium* identified as code number 1002.34, not patented, as the female, or seed, parent with a proprietary selection of *Chrysanthemum×morifolium* identified as code number 98.1911.02, not patented, as the male, or pollen, parent. The new *Chrysanthemum* was discovered and selected by the Inventor as a single flowering plant within the progeny of the stated cross-pollination grown in a controlled environment in Hensbroek, The Netherlands.

Asexual reproduction of the new *Chrysanthemum* by vegetative tip cuttings was first conducted in Hensbroek, The Netherlands on about Dec. 1, 2003. Asexual reproduction by cuttings has shown that the unique features of this new *Chrysanthemum* are stable and reproduced true to type in successive generations.

SUMMARY OF THE INVENTION

The cultivar Serginho has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Serginho'. These characteristics in combination distinguish 'Serginho' as a new and distinct *Chrysanthemum:*

1. Upright, outwardly spreading and mounded plant habit.
2. Freely branching growth habit.
3. Early response time.
4. Decorative-type inflorescences with elliptic-shaped ray florets.
5. Light yellow-colored ray florets.
6. Good postproduction longevity with plants maintaining good substance and color for about one month in an interior environment.

Plants of the new *Chrysanthemum* can be compared to plants of the female parent selection. Plants of the new *Chrysanthemum* differ from plants of the female parent selection in the following characteristics:

1. Plants of the new *Chrysanthemum* flower earlier than plants of the female parent selection.
2. Inflorescences of plants of the new *Chrysanthemum* have darker yellow-colored ray florets than inflorescences of plants of the female parent selection.

Plants of the new *Chrysanthemum* can be compared to plants of the male parent selection. Plants of the new *Chrysanthemum* differ from plants of the male parent selection in the following characteristics:

1. Plants of the new *Chrysanthemum* have thicker stems than plants of the male parent selection.
2. Inflorescences of plants of the new *Chrysanthemum* are more fully double than inflorescences of plants of the male parent selection.
3. Inflorescences of plants of the new *Chrysanthemum* have darker yellow-colored ray florets than inflorescences of plants of the male parent selection.

Plants of the new *Chrysanthemum* can be compared to plants of the cultivar Yoolympia, disclosed in U.S. Plant Pat. No. 14,814. In side-by-side comparisons conducted in Hensbroek, The Netherlands, plants of the new *Chrysanthe-*

*mum* differed from plants of the cultivar Yoolympia in the following characteristics:

1. Leaves of plants of the new *Chrysanthemum* were more pubescent than leaves of plants of the cultivar Yoolympia.
2. Plants of the new *Chrysanthemum* flowered about three to four days earlier than plants of the cultivar Yoolympia.
3. Inflorescences of plants of the new *Chrysanthemum* had fewer ray florets than inflorescences of plants of the cultivar Yoolympia.
4. Plants of the new *Chrysanthemum* and the cultivar Yoolympia differed in ray floret shape and color.

Plants of the new *Chrysanthemum* can also be compared to plants of the cultivar Yoamarillo, disclosed in U.S. Plant Pat. No. 13,970. In side-by-side comparisons conducted in Hensbroek, The Netherlands, plants of the new *Chrysanthemum* differed from plants of the cultivar Yoamarillo in the following characteristics:

1. Plants of the new *Chrysanthemum* were more compact than plants of the cultivar Yoamarillo.
2. Plants of the new *Chrysanthemum* flowered about three to four days earlier than plants of the cultivar Yoamarillo.
3. Inflorescences of plants of the new *Chrysanthemum* had fewer ray florets than inflorescences of plants of the cultivar Yoamarillo.
4. Plants of the new *Chrysanthemum* and the cultivar Yoamarillo differed in ray floret shape.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Serginho'.

The photograph on at the top of the second sheet comprises a top perspective view of typical flowering plants of 'Serginho'.

The photograph at the bottom of the second sheet comprises a close-up view of the upper (left) and lower (right) surfaces of typical inflorescences and leaves of 'Serginho'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown and flowered during the summer in Hensbroek, The Netherlands, in a glass-covered greenhouse and under conditions which approximate those generally used in commercial potted *Chrysanthemum* production. During the production of these plants, day temperatures ranged from 20° C. to 22° C. and night temperatures were about 19° C. Unrooted cuttings were directly stuck in 12-cm containers, exposed to long day/short night conditions, and pinched once about two weeks later. About one week after the pinch, the photoinductive short day/long night treatments were initiated.

Botanical classification: *Chrysanthemum×morifolium* cultivar Serginho.

Commercial classification: Decorative-type potted *Chrysanthemum.*

Parentage:

*Female, or seed, parent.*—Proprietary selection of *Chrysanthemum×morifolium* identified as code number 1002.34, not patented.

*Male, or pollen, parent.*—Proprietary selection of *Chrysanthemum×morifolium* identified as code number 98.1911.02, not patented.

Propagation:

*Type.*—Terminal tip cuttings.

*Time to initiate roots, summer.*—About 5 days at 22° C.

*Time to initiate roots, winter.*—About 7 days at 19° C.

*Time to produce a rooted cutting, summer.*—About 12 days at 22° C.

*Time to produce a rooted cutting, winter.*—About 14 days at 19° C.

*Root description.*—Fine, fibrous; white, close to 155D, in color.

*Rooting habit.*—Freely branching; moderately dense.

Plant description:

*Appearance.*—Herbaceous decorative-type potted *Chrysanthemum* that is typically grown as a disbud-type. Upright with lateral branches outwardly spreading; uniformly mounded crown. Strong, freely branching and vigorous growth habit.

*Plant height.*—About 20 cm to 25 cm.

*Plant width.*—About 30 cm.

*Flowering stems.*—Length: About 15 cm to 20 cm. Diameter: About 4 mm. Strength: Strong. Texture: Pubescent. Color: 146B.

*Foliage description.*—Arrangement: Alternate; simple. Length: About 5 cm to 8 cm. Width: About 3.5 cm to 7 cm. Apex: Apiculate to mucronate. Base: Attenuate. Margin: Palmately lobed. Texture, upper and lower surfaces: Pubescent. Color: Developing foliage, upper surface: Close to 146A. Developing foliage, lower surface: Close to 147B. Fully developed foliage, upper surface: Close to 137A; venation, 146A. Fully developed foliage, lower surface: Close to 147B; venation, 146B. Petiole length: About 1.5 cm. Petiole diameter: About 3.5 mm. Petiole texture, upper and lower surfaces: Pubescent. Petiole color, upper and lower surfaces: Close to 146C.

Inflorescence description:

*Appearance.*—Decorative-type inflorescence form with elliptic-shaped ray florets. Inflorescences borne on terminals above foliage. Disk and ray florets develop acropetally on a capitulum. Inflorescences not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Uniform and early flowering habit; plants exposed to three weeks of long day/short night conditions followed by photoinductive short day/long night conditions flower about 7.5 weeks later.

*Postproduction longevity.*—Inflorescences maintain good color and substance for about one month in an interior environment.

*Quantity of inflorescences.*—About four to six inflorescences per lateral branch.

*Inflorescence bud.*—Height: About 7 mm. Diameter: About 9 mm. Shape: Oblate. Color: 137B.

*Inflorescence diameter.*—About 10 cm to 12 cm.

*Inflorescence height.*—About 2 cm to 3 cm.

*Diameter of disc.*—About 5 mm; inconspicuous.

*Ray florets.*—Length: About 4 cm to 6 cm. Width: About 9 mm to 12 mm. Shape: Elliptic. Apex: Emarginate to praemorse. Base: Attenuate and fused into a corolla tube. Margin: Entire. Orientation: Initially upright to eventually perpendicular. Texture, upper and lower surfaces: Smooth, glabrous; satiny. Number of ray florets per inflorescence: About 160 arranged in numerous whorls. Color: When opening, upper surface: 3A. When opening, lower surface: 5C. Fully opened, upper surface: 4A. Fully opened, lower surface: Closest to 6D.

*Disc florets.*—Arrangement: Massed at center of receptacle. Length: About 4 mm to 6 mm. Diameter: About 1 mm to 1.5 mm. Shape: Tubular; elongated. Apex: Five-pointed. Color: Immature: 21B. Mature, apex: Close to 2A. Mature, mid-section: Close to 21B. Mature, base: 145D.

*Phyllaries.*—Quantity per inflorescence: About 20. Length: About 7 mm. Width: About 2.5 mm. Shape: Lanceolate. Apex: Acute. Base: Truncate. Margin: Entire. Texture, upper surface: Waxy, smooth. Texture, lower surface: Pubescent. Color, upper surface: Close to 146A. Color, lower surface: 137B.

*Reproductive organs.*—Androecium: Present on disc florets only. Anther color: Close to 12A. Pollen amount: None observed. Gynoecium: Present on both ray and disc florets. Stigma color: Close to 145C to 145D.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Serginho', as illustrated and described.

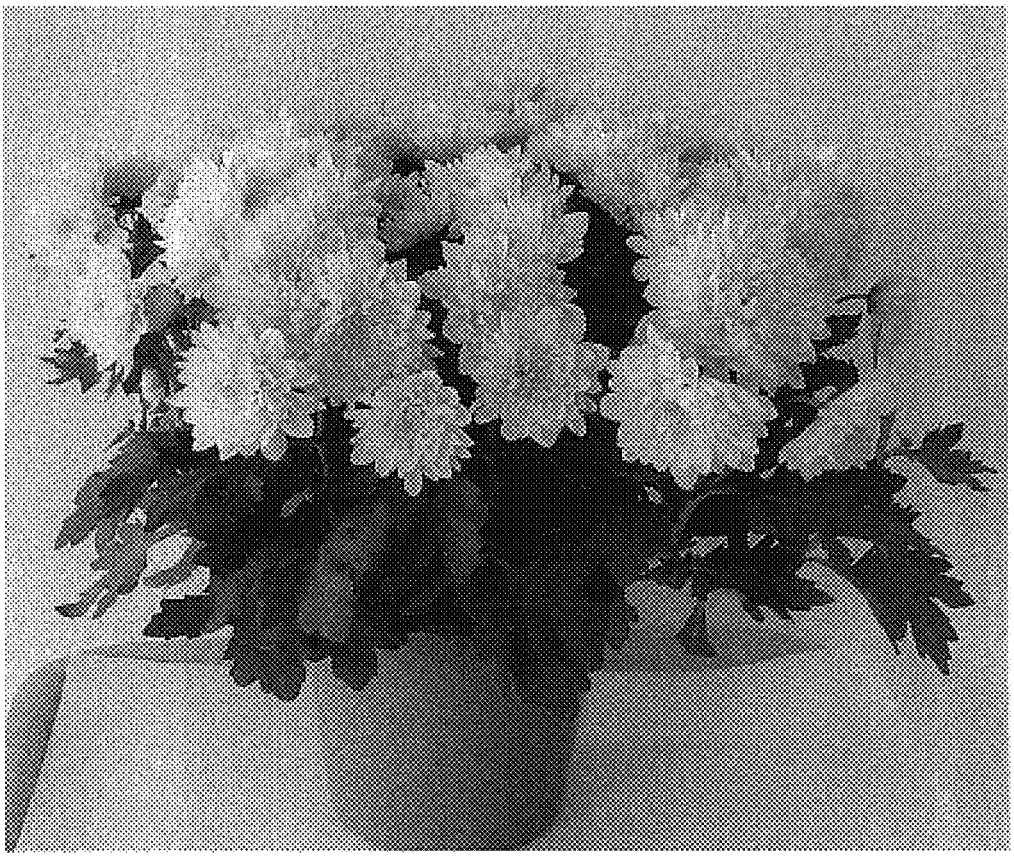

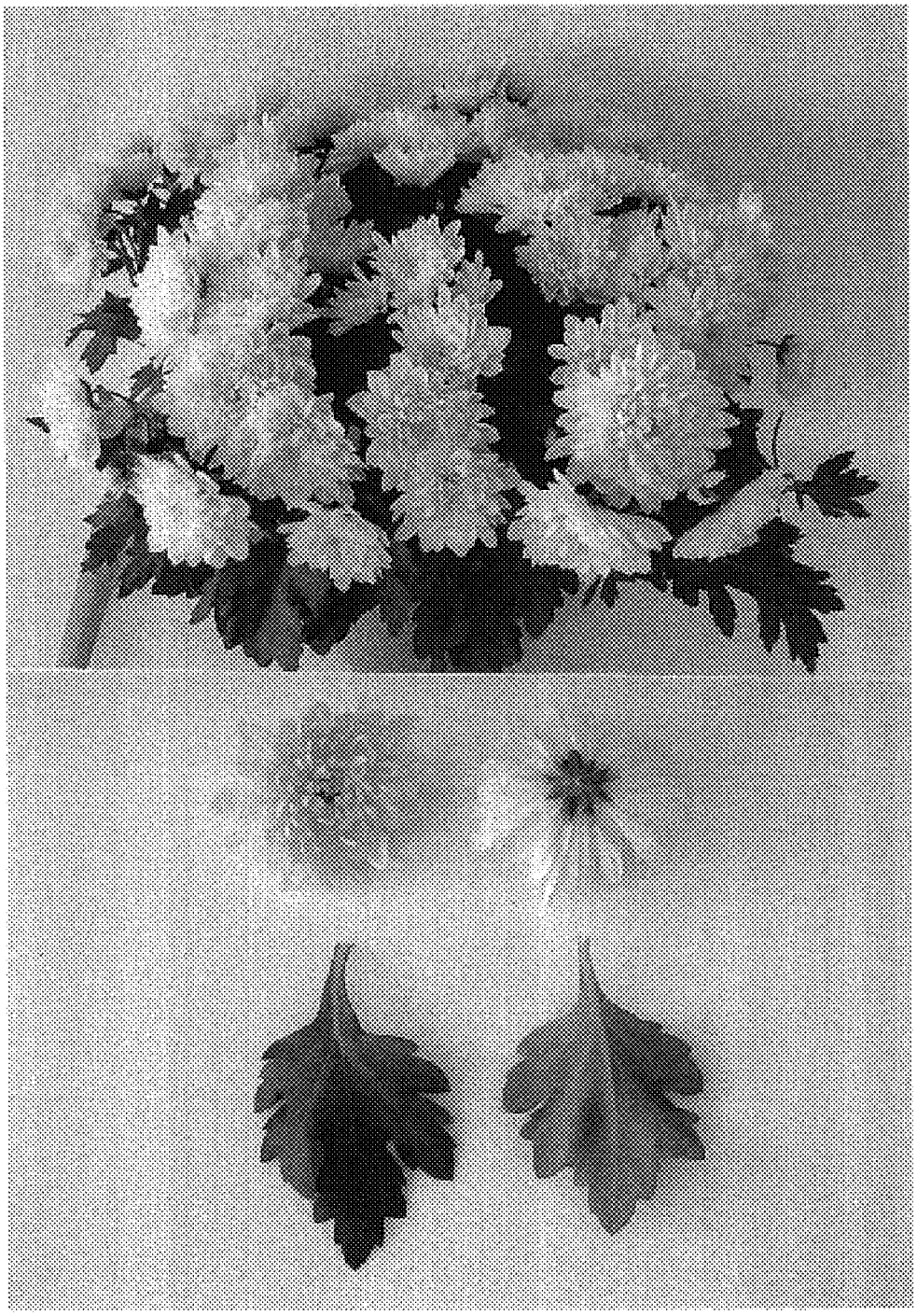

* * * * *